(12) United States Patent
Madden et al.

(10) Patent No.: US 8,999,919 B2
(45) Date of Patent: Apr. 7, 2015

(54) COMPOSITIONS AND METHODS FOR INHIBITING THE INTERACTION BETWEEN CFTR AND CAL

(75) Inventors: Dean R. Madden, Hanover, NH (US); Patrick R. Cushing, East Thetford, VT (US); Prisca Boisguearin, Berlin (DE); Rudolph Volkmer, Nordwestuckermark (DE); Lars Vouilleme, Berlin (DE)

(73) Assignee: Trustees of Dartmouth College, Hanover, NH (US)

( * ) Notice: Subject to any disclaimer, the term of this patent is extended or adjusted under 35 U.S.C. 154(b) by 412 days.

(21) Appl. No.: 13/292,151

(22) Filed: Nov. 9, 2011

(65) Prior Publication Data

US 2012/0071396 A1    Mar. 22, 2012

Related U.S. Application Data

(63) Continuation-in-part of application No. 13/124,470, filed as application No. PCT/US2009/061246 on Oct. 20, 2009, now Pat. No. 8,415,292.

(60) Provisional application No. 61/107,438, filed on Oct. 22, 2008.

(51) Int. Cl.
| | |
|---|---|
| *A61K 38/03* | (2006.01) |
| *A61K 38/08* | (2006.01) |
| *A61P 3/00* | (2006.01) |
| *C07K 4/00* | (2006.01) |
| *C07K 7/04* | (2006.01) |
| *C07K 7/06* | (2006.01) |
| *C07K 7/08* | (2006.01) |
| *A61K 38/00* | (2006.01) |
| *A61K 38/04* | (2006.01) |
| *A61K 38/10* | (2006.01) |
| *C07K 5/103* | (2006.01) |
| *C07K 14/47* | (2006.01) |

(52) U.S. Cl.
CPC ............... *A61K 38/00* (2013.01); *A61K 38/04* (2013.01); *A61K 38/10* (2013.01); *C07K 5/1013* (2013.01); *C07K 14/4703* (2013.01)

(58) Field of Classification Search
CPC ....... A61K 38/10; A61K 38/08; A61K 38/04; A61K 38/03; A61K 38/02; A61K 38/00; C07K 4/00; C07K 7/08; C07K 7/06; C07K 7/04; C07K 7/00
USPC ......................................................... 514/1.8
See application file for complete search history.

(56) References Cited

U.S. PATENT DOCUMENTS

| 2005/0196754 A1 | 9/2005 | Drmanac et al. ............. 435/6.11 |
| 2005/0214791 A1* | 9/2005 | Sheppard et al. ................. 435/6 |
| 2005/0282743 A1 | 12/2005 | Lu et al. .......................... 514/1.2 |
| 2007/0044171 A1 | 2/2007 | Kovalic et al. ................ 800/278 |
| 2008/0069838 A1* | 3/2008 | Peiris et al. |
| 2011/0201544 A1 | 8/2011 | Madden et al. ................ 514/1.8 |

FOREIGN PATENT DOCUMENTS

WO    WO/03/004604    *    1/2003

OTHER PUBLICATIONS

Yamada et al., J. Peptide Res. (2003) 62, 78-87.*
Wolde et al.. The Journal of Biological Chemistry (2007) 282(11), 8099-8108.*
Amacher et al. "Crystallization and Preliminary Diffraction Analysis of the CAL PDZ Domain in Complex with a Selective Peptide Inhibitor" Acta Crystallographica 2011 F67:600-603.
International Search Report from PCT/US2012/063486, Mar. 15, 2013.
Bossard et al. "NHE-RF1 Protein Rescues ΔF508-CFTR Function" American Journal of Physiology—Lung Cellular and Molecular Physiology 2007 292: L1085-L1094.
Chen et al. "Computational Structure-based Redesign of Enzyme Activity" Proceedings of the National Academy of Sciences USA 2009 106(10):3764-3769.
Cheng et al. "A Golgi-associated PDZ Domain Protein Modulates Cystic Fibrosis Transmembrane Regulator Plasma Membrane Expression" The Journal of Biological Chemistry 2002 277(5):3520-3529.
Cushing et al. "The Relative Binding Affinities of PDZ Partners for CFTR: a Biochemical Basis for Efficient Endocytic Recycling" Biochemistry 2008 47(38):10084-10098.
Frey et al. "Predicting Resistance Mutations Using Protein Design Algorithms" Proceedings of the National Academy of Sciences USA 2010 107(31):13707-13712.
Georgiev et al. "The Minimized Dead-end Elimination Criterion and its Application to Protein Redesign in a Hybrid Scoring and Search Algorithm for Computing Partition Functions over Molecular Ensembles" Journal of Computational Chemistry 2008 29(10):1527-1542.
Guerra et al. "Na$^+$/H$^+$Exchanger Regulatory Factor Isoform 1 Overexpression Modulates Cystic Fibrosis Transmembrane Conductance Regulator (CFTR) Expression and Activity in Human Airway 16HBE14o- Cells and Rescues ΔF508 CFTR Functional Expression in Cystic Fibrosis Cells" The Journal of Biological Chemistry 2005 280(49):40925-40933.
Guggino, W.E. and Stanton, B.A. "New Insights into Cystic Fibrosis: Molecular Switches that Regulate CFTR" Nature Reviews Molecular Cell Biology 2006 7(6):426-436.

(Continued)

*Primary Examiner* — Karlheinz R Skowronek
*Assistant Examiner* — Catherine Mader
(74) *Attorney, Agent, or Firm* — Licata & Tyrrell P.C.

(57)    ABSTRACT

The present invention features compositions and methods for increasing the cell surface expression of degradation-prone CFTR proteins and preventing or treating cystic fibrosis. The invention provides peptides and peptidomimetics that selectively inhibit the interaction between CAL and mutant CFTR proteins, thereby stabilizing the CFTR and facilitating transport of the same to the cell surface.

14 Claims, No Drawings

(56) References Cited

OTHER PUBLICATIONS

Leach, A. R. and Lemon, A. P. "Exploring the Conformational Space of Protein Side Chains Using Dead-end Elimination and the A* Algorithm" Proteins: Structure, Function, and Genetics 1998 33:227-239.

Li, C. and Naren, A.P. "Macromolecular Complexes of Cystic Fibrosis Transmembrane Conductance Regulator and its Interacting Partners" Pharmacology & Therapeutics 2005 108(2):208-223.

Piserchio et al. "Association of the Cystic Fibrosis Transmembrane Regulator with CAL: Structural Features and Molecular Dynamics" Biochemistry 2005 44:16158-16166.

Reynolds et al. "Computational Redesign of the SHV-1 β-Lactamase/β-Lactamase Inhibitor Protein Interface" Journal of Molecular Biology 2008 382:1265-1275.

Wolde et al. "Targeting CAL as Negative Regulator of ΔF508-CFTR Cell-Surface Expression" The Journal of Biological Chemistry 2007 282(11):8099-8109.

International Search Report from PCT/US2009/061246, Aug. 25, 2010.

International Preliminary Report on Patentability from PCT/US2009/061246, May 5, 2011.

International Preliminary Report on Patentability from PCT/US2012/063486, May 22, 2014.

\* cited by examiner official
COMPOSITIONS AND METHODS FOR INHIBITING THE INTERACTION BETWEEN CFTR AND CAL This application is a continuation-in-part application of U.S. patent application Ser. No. 13/124,470, filed Apr. 15, 2011 now U.S. Pat. No. 8,415,292, which claims the benefit of priority of PCT/US2009/061246, filed Oct. 20, 2009, and U.S. Provisional Application No. 61/107,438, filed Oct. 22, 2008, which are incorporated herein by reference in their entireties.

This invention was made with government support under grant number R01-DK075309 awarded by the National Institutes of Health. The government has certain rights in the invention. Work on this invention was also supported by grants from the Cystic Fibrosis Foundation.

BACKGROUND OF THE INVENTION

CFTR (Cystic Fibrosis Transmembrane Conductance Regulator) is the target of mutations that cause cystic fibrosis (CF). CF is characterized by abnormal endocrine and exocrine gland function. In CF, unusually thick mucus leads to chronic pulmonary disease and respiratory infections, insufficient pancreatic and digestive function, and abnormally concentrated sweat. Seventy percent of the mutant CFTR alleles in the Caucasian population result from deletion of phenylalanine at position 508 ($\Delta$F508-CFTR), the result of a three base pair deletion in the genetic code. Other mutations have also been described, e.g., a glycine to aspartate substitution at position 551 (G551D-CFTR) occurs in approximately 1% of cystic fibrosis patients.

The $\Delta$F508-CFTR mutation results in a CFTR protein capable of conducting chloride, but absent from the plasma membrane because of aberrant intracellular processing. Under usual conditions (37° C.), the $\Delta$F508-CFTR protein is retained in the endoplasmic reticulum (ER), by prolonged association with the ER chaperones, including calnexin and hsp70. Over expression of $\Delta$F508-CFTR can result in $\Delta$F508-CFTR protein appearing at the cell surface, and this protein is functional once it reaches the cell surface. The $\Delta$F508-CFTR "trafficking" block is also reversible by incubation of cultured CF epithelial cells at reduced temperatures (25-27° C.). Lowered temperature results in the appearance of CFTR protein and channel activity at the cell surface, suggesting an intrinsic thermodynamic instability in $\Delta$F508-CFTR at 37° C. that leads to recognition of the mutant protein by the ER quality control mechanism, prevents further trafficking, and results in protein degradation. Chemical chaperones are currently being developed to restore the folding of $\Delta$F508-CFTR. However, when $\Delta$F508-CFTR is expressed at the cell-surface following treatment, CAL (also known as CFTR-associated ligand, PIST, GOPC, ROS, and FIG) directs the lysosomal degradation of CFTR in a dose-dependent fashion and reduces the amount of CFTR found at the cell surface. Conversely, NHERF1 and NHERF2 functionally stabilize CFTR. Consistent with this role of CAL, RNA interference targeting of endogenous CAL also increases cell-surface expression of the disease-associated $\Delta$F508-CFTR mutant and enhances transepithelial chloride currents in a polarized human patient bronchial epithelial cell line (Wolde, et al. (2007) *J. Biol. Chem.* 282:8099-8109).

Current treatments for cystic fibrosis generally focus on controlling infection through antibiotic therapy and promoting mucus clearance by use of postural drainage and chest percussion. However, even with such treatments, frequent hospitalization is often required as the disease progresses.

New therapies designed to increase chloride ion conductance in airway epithelial cells have been proposed, and restoration of the expression of functional CFTR at the cell surface is considered a major therapeutic goal in the treatment of cystic fibrosis, a disease that affects ~30,000 patients in the U.S., and ~70,000 patients worldwide. Indeed, screening assays have been described for identifying agents that modify or restore cell surface expression of mutant CFTR proteins. However, only a limited number of "corrector" drugs has been described for the treatment of CF. In addition, U.S. Patent Application No. 20050282743 discloses reagents and methods for inhibiting interactions between proteins in cells, particularly interactions between a PDZ protein such as PIST and a PL protein such as wild-type CFTR. However, no high-affinity and selective inhibitor compounds have been identified for PIST, nor have PIST reporter sequences been identified that would permit small-molecule screening, nor have any such compounds been shown to have efficacy in stabilizing mutant, degradation-prone CFTR. Accordingly, improvements are needed in the treatment of cystic fibrosis. The present invention fulfills this need and further provides other related advantages.

SUMMARY OF THE INVENTION

The present invention features methods for increasing cell surface expression of a degradation-prone Cystic Fibrosis Transmembrane Conductance Regulator (CFTR) protein and a method of preventing or treating CF in a subject in need of treatment. The methods of the invention employ an agent that selectively inhibits the interaction between the degradation-prone CFTR and CFTR-Associated Ligand (CAL) thereby increasing cell surface expression of the degradation-prone CFTR protein. In one embodiment, the degradation-prone CFTR is $\Delta$F508 CFTR or R1066C CFTR. In other embodiments of the invention, the agent is a peptide or peptidomimetic of 6 to 20 residues in length. In certain embodiments, the peptide comprises the amino acid sequence of SEQ ID NO:1 or SEQ ID NO:24, or a derivative thereof. In particular embodiments, the peptide is listed in Table 1. In another embodiment, the peptidomimetic is a mimetic of the amino acid sequence of SEQ ID NO:1. In a further embodiment, the peptidomimetic is listed in Table 2.

Peptides, derivatives, peptidomimetic, as well as compositions containing the same are also provided.

DETAILED DESCRIPTION OF THE INVENTION

Novel inhibitors have now been identified that block the interaction or binding of CFTR with the CAL PDZ binding site by competitive displacement. By inhibiting this interaction with CAL, degradation-prone CFTR proteins are stabilized and the amount of CFTR protein at the cell surface is effectively increased. Indeed, representative peptide and peptidomimetic CAL inhibitors were shown to increase the apical cell-surface expression and transepithelial chloride efflux of the most common CFTR mutation associated with CF. Accordingly, inhibitors of the present invention find application in increasing the cell surface expression of degradation-prone CFTR proteins and in the treatment for CF. As used herein, "cell surface expression" of a CFTR protein refers to CFTR protein which has been transported to the surface of a cell. In this regard, an agent that increases the cell surface expression of a CFTR protein refers to an agent that increases the amount of CFTR protein, which is present or detected at the plasma membrane of a cell, as compared to a cell which is not contacted with the agent.

Genetic, biochemical, and cell biological studies have revealed a complex network of protein-protein interactions that are required for correct CFTR trafficking, including a number of PDZ (PSD-95, discs-large, zonula occludens-1) proteins, which act as adaptor molecules, coupling CFTR to other components of the trafficking and localization machinery, and to other transmembrane channels and receptors (Kunzelmann (2001) *News Physiol. Sci.* 16:167-170; Guggino & Stanton (2006) *Nat. Rev. Mol. Cell. Biol.* 7:426-436). Class I PDZ domains typically recognize C-terminal binding motifs characterized by the sequence -(Ser/Thr)-X-Φ-COOH (where represents a hydrophobic side chain, and X represents any amino acid) (Harris & Lim (2001) *J. Cell Sci.* 114:3219-3231; Brône & Eggermont (2005) *Am. J. Physiol.* 288:C20-C29). The cytoplasmic C-terminus of CFTR satisfies the class I PDZ binding motif, ending in the sequence -Thr-Arg-Leu (Hall, et al. (1998) *Proc. Natl. Acad. Sci. USA* 95:8496-8501; Short, et al. (1998) *J. Biol. Chem.* 273:19797-19801; Wang, et al. (1998) *FEBS Lett.* 427:103-108) and it has been demonstrated that CFTR C-terminal PDZ-binding motif controls retention of the protein at the apical membrane and modulates its endocytic recycling (Moyer, et al. (2000) *J. Biol. Chem.* 275:27069-27074; Swiatecka-Urban, et al. (2002) *J. Biol. Chem.* 277:40099-40105). PDZ proteins that have been shown to bind or interact with CFTR include NHERF1 (Na+/H+ exchanger regulatory factor 1; also known as EBP50), NHERF2 (Na+/H+ exchanger regulatory factor 2, also known as E3KARP), NHERF3 (Na+/H+ exchanger regulatory factor 3, also known as CAP70, PDZK1, or NaPi CAP-1), NHERF4 (Na+/H+ exchanger regulatory factor 4, also known as IKEPP or NaPi CAP-2), and CAL (CFTR-associated ligand; also known as PIST, GOPC, and FIG; GENBANK Accession Nos. NP_065132 and NP_001017408, incorporated herein by reference) (Guggino & Stanton (2006) supra; Li & Naren (2005) *Pharmacol. Ther.* 108:208-223). Of these proteins, CAL has been shown to reduce the levels of recombinant wild-type CFTR found in whole cell lysates and at the cell surface, whereas overexpression of NHERF1 together with CAL can block this effect on both wild-type and ΔF508-CFTR (Cheng, et al. (2002) *J. Biol. Chem.* 277:3520-3529; Guerra, et al. (2005) *J. Biol. Chem.* 280:40925-40933). Moreover, RNAi targeting of endogenous CAL specifically increases cell surface expression of the ΔF508-CFTR mutant protein and enhances transepithelial chloride currents in a polarized human patient bronchial epithelial cell line (Wolde, et al. (2007) *J. Biol. Chem.* 282:8099-8109). These data indicate that the PDZ proteins which interact with CFTR have opposing functions. Thus, targeting the interaction of CAL with CFTR can stabilize a mutant CFTR protein and facilitate cell surface expression of the same.

The CFTR protein and mutants thereof are well-known in the art and wild-type human CFTR is disclosed in GENBANK Accession No. NP_000483, incorporated herein by reference. Misfolding of mutant CFTR proteins has been shown to dramatically augment the ubiquitination susceptibility of the protein in post-Golgi compartments (Swiatecka-Urban, et al. (2005) *J. Biol. Chem.* 280:36762). Thus, for the purposes of the present invention, the term "degradation-prone" when used as a modifier of a CFTR protein, refers to a mutant CFTR protein that exhibits an increased rate of degradation following initial trafficking to the cell surface and a decrease in the amount of CFTR protein present at the cell surface (i.e., plasma membrane). Examples of degradation-prone CFTR proteins include, but are not limited to ΔF508 CFTR and Δ70F CFTR (see Sharma, et al. (2004) *J. Cell Biol.* 164:923). Other degradation-prone CFTR proteins are known in the art and/or can be identified by routine experimentation.

For example, the rate or amount of transport of CFTR protein from the cell surface can be determined by detecting the amount of complex-glycosylated CFTR protein present at the cell surface, in endoplasmic vesicles and/or in lysosomes using methods such as cell surface immunoprecipitation or biotinylation or cell immunocytochemistry with an antibody specific for CFTR protein. Additional methods, both in vivo and in vitro, are known in the art that can be used for detecting an increase or decrease in cell surface expression of a CFTR protein.

Because PDZ proteins share overlapping specificities, particular embodiments of this invention embrace inhibitory agents that selectively block the interaction or binding between a degradation-prone CFTR and CAL. As used herein, a "selective inhibitor of the CFTR and CAL interaction" or "an agent that selectively inhibits the interaction between the degradation-prone CFTR and CAL" is any molecular species that is an inhibitor of the CFTR and CAL interaction but which fails to inhibit, or inhibits to a substantially lesser degree the interaction between CFTR and proteins that stabilize degradation-prone CFTR, e.g., NHERF1 AND NHERF2. Methods for assessing the selectively of an inhibitor of the CFTR and CAL interaction are disclosed herein and can be carried out in in vitro or in vivo assays.

By way of illustration, libraries of agents were screened for the ability to increase the amount of ΔF508 CFTR at the apical membrane and to increase the CFTR-mediated chloride efflux across monolayers of CFBE410-cells. The magnitude of the functional rescue of the mutant CFTR protein correlated with the selectivity of the agent for CAL versus NHERF1 and NHERF2, namely, the more selective the agent for the CAL binding site, the more effective the agent was at enhancing chloride efflux. Moreover, upon further refinement, off-site targets were eliminated by modification of the amino acid residue at $P^{-5}$ (see Example 4).

Accordingly, the present invention features compositions and methods for facilitating the cell surface expression of mutant CFTR by selectively blocking the interaction between a degradation-prone CFTR and CAL. Agents of the present invention can be any molecular species, with particular embodiments embracing peptides or mimetics thereof.

As used herein, the term "peptide" denotes an amino acid polymer that is composed of at least two amino acids covalently linked by an amide bond. Peptides of the present invention are desirably 6 to 20 residues in length, or more desirably 7 to 15 residues in length. In certain embodiments, a selective inhibitor of the CFTR and CAL interaction is a 6 to 20 residue peptide containing the amino acid sequence $Xaa_1$-$Xaa_2$-$Xaa_3$-$Xaa_4$-$Xaa_5$-$Xaa_6$ (SEQ ID NO:1), wherein $Xaa_1$ is Met, Phe, Leu, Ala or Trp; $Xaa_2$ is Gln, Pro, or Phe; $Xaa_3$ is Ser, Val or Thr; $Xaa_4$ is Ser or Thr; $Xaa_5$ is Lys, Arg or Ile; and $Xaa_6$ is Ile or Val. In certain embodiments of the present invention, a selective inhibitor of the CFTR and CAL interaction is a peptide having an amino acid sequence as listed in Table 1.

TABLE 1

| Peptide Designation | Peptide Sequence | SEQ ID NO: |
|---|---|---|
| PRC 01 | CANGLMQTSKI | 2 |
| PRC 02 | CGLMQTSKI | 3 |
| PRC 03 | CFFSTII | 4 |
| PRC 04 | CFFSTII | 5 |
| PRC 05 | CMQTSII | 6 |
| PRC 06 | CMQTSKI | 7 |
| PRC 07 | CWQTSII | 8 |
| PRC 08 | CWPTSII | 9 |

TABLE 1-continued

| Peptide Designation | Peptide Sequence | SEQ ID NO: |
|---|---|---|
| PRC 09 | CTWQTSII | 10 |
| PRC 10 | CKWQTSII | 11 |
| PRC 11 | PHWQTSII | 12 |
| PRC 12 | FHWQTSII | 13 |
| PRC 13 | SRWQTSII | 14 |
| PRC 17 | CANSRWQTSII | 15 |
| PRC 25 | GLWPTSII | 16 |
| PRC 26 | SRWPTSII | 17 |
| PRC 27 | FPWPTSII | 18 |
| PRC 30 or F*-iCal36 | *FITC-ANSRWPTSII | 19 |
| PRC 36 or iCal36 | ANSRWPTSII | 20 |
| iCAL42 | ANSRLPTSII | 21 |
|  | ANSRAPTSII | 22 |
| kCAL01 | WQVTRV | 23 |

FITC = fluorescein.

In particular embodiments of the present invention, a selective inhibitor of the CFTR and CAL interaction is a peptide that binds to CAL, but fails to bind to any other lung epithelial cell protein containing a PDZ domain including but not limited to TIP-1, NHERF1 and NHERF2. In accordance with this embodiment, the inhibitor is "CAL selective." CAL selective inhibitors are desirably 6 to 20 residue peptide and contain the amino acid sequence $Xaa_7$-$Xaa_8$-$Xaa_8$-$Xaa_{10}$-$Xaa_n$-$Xaa_{12}$ (SEQ ID NO:24), wherein $Xaa_7$ is Met, Phe, Leu, or Ala; $Xaa_8$ is Gln, Pro, or Phe; $Xaa_8$ is Ser, Val or Thr; $Xaa_{10}$ is Ser or Thr; $Xaa_{11}$ is Lys, Arg or Ile; and $Xaa_{12}$ is Ile or Val. In specific embodiments, a CAL selective inhibitor is a peptide of SEQ ID NO:21 or SEQ ID NO:22.

In accordance with the present invention, derivatives of the peptides of the invention are also provided. As used herein, a peptide derivative is a molecule which retains the primary amino acids of the peptide, however, the N-terminus, C-terminus, and/or one or more of the side chains of the amino acids therein have been chemically altered or derivatized. Such derivatized peptides include, for example, naturally occurring amino acid derivatives, for example, 4-hydroxyproline for proline, 5-hydroxylysine for lysine, homoserine for serine, ornithine for lysine, and the like. Other derivatives or modifications include, e.g., a label, such as fluorescein or tetramethylrhodamine; or one or more post-translational modifications such as acetylation, amidation, formylation, hydroxylation, methylation, phosphorylation, sulfatation, glycosylation, or lipidation. Indeed, certain chemical modifications, in particular N-terminal glycosylation, have been shown to increase the stability of peptides in human serum (Powell et al. (1993) *Pharma. Res.* 10:1268-1273). Peptide derivatives also include those with increased membrane permeability obtained by N-myristoylation (Brand, et al. (1996) *Am. J. Physiol. Cell. Physiol.* 270:C1362-C1369). An exemplary peptide derivative is provided in SEQ ID NO:19 (Table 1).

In addition, a peptide derivative of the invention can include a cell-penetrating sequence which facilitates, enhances, or increases the transmembrane transport or intracellular delivery of the peptide into a cell. For example, a variety of proteins, including the HIV-1 Tat transcription factor, *Drosophila* Antennapedia transcription factor, as well as the herpes simplex virus VP22 protein have been shown to facilitate transport of proteins into the cell (Wadia and Dowdy (2002) *Curr. Opin. Biotechnol.* 13:52-56). Further, an arginine-rich peptide (Futaki (2002) *Int. J. Pharm.* 245:1-7), a polylysine peptide containing Tat PTD (Hashida, et al. (2004) *Br. J. Cancer* 90(6):1252-8), Pep-1 (Deshayes, et al. (2004) *Biochemistry* 43(6):1449-57) or an HSP70 protein or fragment thereof (WO 00/31113) is suitable for enhancing intracellular delivery of a peptide or peptidomimetic of the invention into the cell. An exemplary cell penetrating peptide is shown in Table 2 and provided as SEQ ID NO:34.

While a peptide of the invention can be derivatized with by one of the above indicated modifications, it is understood that a peptide of this invention may contain more than one of the above described modifications within the same peptide.

As indicated, the present invention also encompasses peptidomimetics of the peptides disclosed herein. Peptidomimetics refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the activity of the mimetic. Routine testing can be used to determine whether a mimetic has the requisite activity, e.g., that it can inhibit the interaction between CFTR and CAL. The phrase "substantially the same," when used in reference to a mimetic or peptidomimetic, means that the mimetic or peptidomimetic has one or more activities or functions of the referenced molecule, e.g., selective inhibition of the CAL and CFTR interaction.

There are clear advantages for using a mimetic of a given peptide. For example, there are considerable cost savings and improved patient compliance associated with peptidomimetics, since they can be administered orally compared with parenteral administration for peptides. Furthermore, peptidomimetics are much cheaper to produce than peptides.

Thus, peptides described above have utility in the development of such small chemical compounds with similar biological activities and therefore with similar therapeutic utilities. The techniques of developing peptidomimetics are conventional. For example, peptide bonds can be replaced by non-peptide bonds or non-natural amino acids that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to a CAL protein, by NMR spectroscopy, crystallography and/or computer-aided molecular modeling. These techniques aid in the development of novel compositions of higher potency and/or greater bioavailability and/or greater stability than the original peptide (Dean (1994) *BioEssays* 16:683-687; Cohen & Shatzmiller (1993) *J. Mol. Graph.* 11:166-173; Wiley & Rich (1993) *Med. Res. Rev.* 13:327-384; Moore (1994) *Trends Pharmacol. Sci.* 15:124-129; Hruby (1993) *Biopolymers* 33:1073-1082; Bugg, et al. (1993) *Sci. Am.* 269:92-98). Once a potential peptidomimetic compound is identified, it may be synthesized and assayed using an assay described herein or any other appropriate assay for monitoring cell surface expression of CFTR.

It will be readily apparent to one skilled in the art that a peptidomimetic can be generated from any of the peptides described herein. It will furthermore be apparent that the peptidomimetics of this invention can be further used for the development of even more potent non-peptidic compounds, in addition to their utility as therapeutic compounds.

Peptide mimetic compositions can contain any combination of non-natural structural components, which are typically from three structural groups: residue linkage groups other than the natural amide bond ("peptide bond") linkages; non-natural residues in place of naturally occurring amino acid residues; residues which induce secondary structural mimicry, i.e., induce or stabilize a secondary structure, e.g., a beta turn, gamma turn, beta sheet, alpha helix conformation, and the like; or other changes which confer resistance to proteolysis. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH—CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins,* 7:267-357, "Peptide and Backbone Modifications," Marcel Decker, N.Y.).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenyl-phenylalanine; and D- or L-2-indole (alkyl)alanines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic ring include, for example, thiazolyl, thiophenyl, pyrazolyl, benzimidazolyl, naphthyl, furanyl, pyrrolyl, and pyridyl aromatic rings.

Cyclic peptides or cyclized residue side chains also decrease susceptibility of a peptide to proteolysis by exopeptidases or endopeptidases. Thus, certain embodiments embrace a peptidomimetic of the peptides disclosed herein, whereby one or more amino acid residue side chains are cyclized according to conventional methods.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N=C=N—R') including, for example, 1-cyclohexyl-3(2-morpholinyl-(4-ethyl) carbodiimide or 1-ethyl-3 (4-azonia-4,4-dimetholpentyl) carbodiimide. Aspartyl or glutamyl groups can also be converted to asparaginyl and glutaminyl groups by reaction with ammonium ions.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, dehydroproline, 3- or 4-methylproline, and 3,3,-dimethylproline.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

As will be appreciated by one skilled in the art, the peptidomimetics of the present invention can also include one or more of the modifications described herein for derivatized peptides, e.g., a label, one or more post-translational modifications, or cell-penetrating sequence.

As with peptides of the invention, peptidomimetics are desirably 6 to 20 residues in length, or more desirably to 15 residues in length. In certain embodiments, a selective inhibitor of the CFTR and CAL interaction is a 6 to 20 residue peptidomimetic based on the amino acid sequence of SEQ ID NO:1 or SEQ ID NO:24. In certain embodiments of the present invention, a selective inhibitor of the CFTR and CAL interaction is a peptidomimetic listed in Table 2.

TABLE 2

| Peptide Designation | Peptide Sequence | SEQ ID NO: |
|---|---|---|
| PRC 21 | WrFK(K-FITC)-ANSRWPTSII | 25 |
| PRC 23 | WrFKK-ANSRWPTSII | 26 |
| PRC 29 | WrFK(K-ROX)-ANSRWPTSII | 27 |
| PRC 37 | pneaWPTSII | 28 |
| B1 | fNaRWQTSII | 29 |
| B2 | fNSRWQTSII | 30 |
| B3 | knSRWQTSII | 31 |
| B4 | pnSRWQTSII | 32 |
| A6 | AnSRWQTSII | 33 |

Lower-case = D-amino acids;
FITC = fluorescein;
ROX = 6-carboxy-X-rhodamine.
Underlined residues indicate cyclized side chains. WrFKK (SEQ ID NO: 34) is a cell penetrating peptide.

Also included with the scope of the invention are peptides and peptidomimetics that are substantially identical to a sequence set forth herein, in particular SEQ ID NO:1 or SEQ ID NO:24. The term "substantially identical," when used in reference to a peptide or peptidomimetic, means that the sequence has at least 75% or more identity to a reference sequence (e.g., 80%, 85%, 90%, 95%, 96%, 97%, 98%, 99%). The length of comparison sequences will generally be at least 5 amino acids, but typically more, at least 6 to 10, 7 to 15, or 8 to 20 residues. In one aspect, the identity is over a defined sequence region, e.g., the amino or carboxy terminal 3 to 5 residues.

The peptides, derivatives and peptidomimetics can be produced and isolated using any method known in the art. Peptides can be synthesized, whole or in part, using chemical methods known in the art (see, e.g., Caruthers (1980) *Nucleic Acids Res. Symp. Ser.* 215-223; Horn (1980) *Nucleic Acids Res. Symp. Ser.* 225-232; and Banga (1995) *Therapeutic Peptides and Proteins, Formulation, Processing and Delivery Systems,* Technomic Publishing Co., Lancaster, Pa.). Peptide synthesis can be performed using various solid-phase techniques (see, e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the manufacturer's instructions.

Individual synthetic residues and peptides incorporating mimetics can be synthesized using a variety of procedures and methodologies known in the art (see, e.g., *Organic Syntheses Collective Volumes*, Gilman, et al. (Eds) John Wiley & Sons, Inc., NY). Peptides and peptide mimetics can also be synthesized using combinatorial methodologies. Techniques for generating peptide and peptidomimetic libraries are well-known, and include, for example, multipin, tea bag, and split-couple-mix techniques (see, for example, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; and Ostresh (1996) *Methods Enzymol.* 267:220-234). Modified peptides can be further produced by chemical modification methods (see, for example, Belousov (1997) *Nucleic Acids Res.* 25:3440-3444; Frenkel (1995) *Free Radic. Biol. Med.* 19:373-380; and Blommers (1994) *Biochemistry* 33:7886-7896).

Alternatively, peptides of this invention can be prepared in recombinant protein systems using polynucleotide sequences encoding the peptides. By way of illustration, a nucleic acid molecule encoding a peptide of the invention is introduced into a host cell, such as bacteria, yeast or mammalian cell, under conditions suitable for expression of the peptide, and the peptide is purified or isolated using methods known in the art. See, e.g., Deutscher et al. (1990) *Guide to Protein Purification: Methods in Enzymology* Vol. 182, Academic Press.

It is contemplated that the peptides and mimetics disclosed herein can be used as lead compounds for the design and synthesis of compounds with improved efficacy, clearance, half-lives, and the like. One approach includes structure-activity relationship (SAR) analysis (e.g., NMR analysis) to determine specific binding interactions between the agent and CAL or CFTR to facilitate the development of more efficacious agents. Agents identified in such SAR analysis or from agent libraries can then be screened for their ability to increase cell surface expression of CFTR.

In this regard, the present invention also relates to a method for identifying an agent for which facilitates cell surface expression of a degradation-prone CFTR. The method of the invention involves contacting CAL with a test agent under conditions allowing an interaction between the agent and CAL, and determining whether the agent competitively displaces binding of a degradation-prone CFTR to CAL. Particular degradation-prone CFTRs that can be used include, but are not limited to, ΔF508 and R1066C.

In one embodiment, the method is performed in vivo. Various detection methods can be employed to determine whether the agent displaces CFTR from CAL. For example, displacement can be based on detecting an increase in an amount of CFTR protein on the cell surface, immunostaining with a specific antibody (e.g., anti-CFTR, M3A7), or direct visualization (e.g., a CFTR-GFP fusion). Additional methods useful for determining whether there is an increase in cell surface protein included cell panning. In cell panning assays, plates are coated with an antibody that binds to the cell surface protein. The number of cells that binds to the antibody coated plate corresponds to an amount of protein on the cell surface.

In another embodiment, the method is performed in vitro. In accordance with this embodiment, a combination of peptide-array screening and fluorescence polarization is used to identify agents that bind to an isolated, recombinant CAL PZD domain. For example, it contemplated that the high-affinity CAL-binding peptides disclosed herein can be use as reporters for small-molecule screening assays, wherein the small molecules compete for binding to the CAL PZD domain. The ability to target PDZ proteins selectively, using a combination of peptide-array screening and fluorescence-polarization assays on purified, recombinant PDZ domains, represents a novel achievement, due to the bi-directional promiscuity of PDZ:protein interactions. Since PDZ proteins are implicated in the trafficking and intracellular localization of many disease-related receptors, selective targeting may provide an important tool for identifying additional PDZ-based therapeutics.

In so far as it is desirable that the agent selectively inhibit the interaction between CAL and CFTR, a further embodiment of this invention embraces contacting NHERF1 and/or NHERF2 with an identified inhibitor of the CAL and CFTR interaction and determining whether the agent competitively displaces binding to NHERF1 and/or NHERF2. Agents that fail to inhibit, or inhibit to a substantially lesser degree the interaction between CFTR and NHERF1 or NHERF2 as compared to CAL, would be considered selective.

Agents which can be screened in accordance with the methods disclosed herein can be from any chemical class including peptides, antibodies, small organic molecules, carbohydrates, etc.

Agents specifically disclosed herein, as well as derivatives, and peptidomimetics of said agents and agents identified by design and/or screening assays find application in increasing in the cell surface expression of degradation-prone CFTR proteins and in the treatment of CF. Thus, methods for increasing the cell surface expression of a degradation-prone CFTR and treating cystic fibrosis are also provided by this invention.

In accordance with one embodiment, the cell surface expression of a degradation-prone CFTR protein is enhanced or increased by contacting a cell expressing a degradation-prone CFTR with an agent that decreases or inhibits the interaction between the CFTR protein and CAL so that the cell surface expression of the CFTR protein is increased or enhanced. Desirably, the agent is administered in an amount that effectively stabilizes the degradation-prone CFTR protein and increases the amount of said CFTR protein present or detectable at the cell surface by at least 60%, 70%, 80%, 90%, 95%, 99% or 100% as compared to cells not contacted with the agent. Any cell can be employed in this method of the invention so long as it expresses a degradation-prone CFTR. Specific examples of such cells include, but are not limited to, primary cells of a subject with CF or cultured airway epithelial cell lines derived from a CF patient's bronchial epithelium (e.g., CFBE41O-). It is contemplated that this method of the invention can be used to increase cell surface expression of a degradation-prone CFTR protein in a human subject as well as increase the cell surface expression of a degradation-prone CFTR protein in an isolated cell or cell culture to, e.g., study the transport and/or activity of the mutant protein at the cell surface.

In another embodiment, a subject with CF or at risk of CF is treated with one or more the agents of the invention. In accordance with this embodiment, an effective amount of an agent that selectively inhibits the interaction between a degradation-prone CFTR and CAL is administered to a subject in need of treatment thereby preventing or treating the subject's cystic fibrosis. Subjects benefiting from treatment with an agent of the invention include subjects confirmed as having CF, subjects suspected of having CF, or subjects at risk of having CF (e.g., subjects with a family history). In one aspect, the subject expresses a degradation-prone CFTR, such as ΔF508 or R1066C CFTR. Other CFTR mutant sequences are also known in the art including, for example, ΔI507, N1303K, S549I, S549R, A559T, H139R, G149R, D192G, R258G, S949L, H949Y, H1054D, G1061R, L1065P, R1066C, R1066H, R1066L, Q1071P, L 1077P, H1085R, W1098R, M1101K, M1101R.

Successful clinical use of a selective inhibitor of the invention can be determined by the skilled clinician based upon routine clinical practice, e.g., by monitoring frequency of respiratory infections and/or coughing; or changes in breathing, abdominal pain, appetite, and/or growth according to methods known in the art.

Agents disclosed herein can be employed as isolated molecules (i.e., isolated peptides, derivatives, or peptidomimetics), or in the case of peptides, be expressed from nucleic acids encoding said peptides. Such nucleic acids can, if desired, be naked or be in a carrier suitable for passing through a cell membrane (e.g., DNA-liposome complex), contained in a vector (e.g., plasmid, retroviral vector, lentiviral, adenoviral or adeno-associated viral vectors and the like), or linked to inert beads or other heterologous domains (e.g., antibodies, biotin, streptavidin, lectins, etc.), or other appropriate compositions. Thus, both viral and non-viral means of nucleic acid delivery can be achieved and are contemplated. Desirably, a vector used in accordance with the invention provides all the necessary control sequences to facilitate expression of the peptide. Such expression control sequences can include but are not limited to promoter sequences, enhancer sequences, etc. Such expression control sequences, vectors and the like are well-known and routinely employed by those skilled in the art.

For example, when using adenovirus expression vectors, the nucleic acid molecule encoding a peptide can be ligated to an adenovirus transcription/translation control complex, e.g., the late promoter and tripartite leader sequence. Alternatively, the vaccinia virus 7.5K promoter can be used. (see e.g., Mackett, et al. (1982) *Proc. Natl. Acad. Sci. USA* 79:7415-7419; Mackett, et al. (1984) *J. Virol.* 49:857-864; Panicali, et al. (1982) *Proc. Natl. Acad. Sci. USA* 79:4927-4931). Mammalian expression systems further include vectors specifically designed for "gene therapy" methods including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO 92/05266 and WO 92/14829).

Moreover, agents of the invention can be combined with other agents employed in the treatment of CF, including molecules which ameliorate the signs or symptoms of CF. Such agents include, but are not limited to, nonsteroidal anti-inflammatory drugs or steroids, such as ibuprofen for treating inflammation; pentoxifylline for decreasing inflammation; dornase alfa for treating airway blockage due to mucus buildup or certain flavones and isoflavones, which are capable of stimulating CFTR-mediated chloride transport in epithelial tissues in a cyclic-AMP independent manner (U.S. Pat. No. 6,329,422); 2,2-dimethyl butyric acid (U.S. Pat. No. 7,265,153); glycerol, acetic acid, butyric acid, D- or L-amino-n-butyric acid, alpha- or beta-amino-n-butyric acid, arginine butyrate or isobutyramide, all disclosed in U.S. Pat. Nos. 4,822,821 and 5,025,029; butyrin, 4-phenyl butyrate, phenylacetate, and phenoxy acetic acid, disclosed in U.S. Pat. No. 4,704,402, wherein in combination with one or more agents of this invention, an additive or synergistic effect is achieved.

For therapeutic use, agents of the invention (including nucleic acids encoding peptides) can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Compositions of the present invention can be administered parenterally (for example, by intravenous, intraperitoneal, subcutaneous or intramuscular injection), topically including via inhalation, transdermally, orally, intranasally, intravaginally, or rectally according to standard medical practices.

The selected dosage level of an agent will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician having ordinary skill in the art can readily determine and prescribe the effective amount of the pharmaceutical composition required based upon the administration of similar compounds or experimental determination. For example, the physician could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The fact that other proteins destined for the intracellular transport pathway frequently exhibit transport delays due to mutations, or other factors, indicates that the cell-surface expression of such degradation-prone proteins may also be mediated by CAL. Thus, it is contemplated that the agents of this invention can also be used to induce or increase the cell surface expression of other degradation-prone proteins. Accordingly, physiological disorders associated with other degradation-prone proteins besides CFTR can similarly be treated using the methods disclosed herein. Physiological disorders associated with a degradation-prone protein that can be treated in a method of the invention include, for example, Stargardt's disease and particular types of macular dystrophy caused by mutations of the retinal rod transporter, ABC-R, resulting in deficiency of export.

The invention is described in greater detail by the following non-limiting examples.

Example 1

Materials and Methods

Protein Expression and Purification.

CALP (UniProt Accession No. Q9HD26-2) was expressed and purified (Cushing, et al. (2008) Biochemistry 47:10084-10098). TIP-1 (Accession No. O14907) was expressed and purified similarly except that an N-terminal $His_{10}$ tag was used with a HRV 3C protease recognition sequence (LEVLFQ*G; SEQ ID NO:35) upstream of the full-length protein sequence. Following TIP-1 purification via immobilized metal-affinity chromatography, the protein was injected onto a SUPERDEX S75 gel filtration column (GE Healthcare) equilibrated in 50 mM Tris pH 8.5, 150 mM NaCl, 0.1 mM TCEP, 0.02% $NaN_3$. Human rhinovirus 3C protease (Novagen) was added to the protein at a 1:30 mass ratio and incubated at 4° C. for 48 hours. Following cleavage, the protein was passed through a 1 mL HISTRAP HP column (GE Healthcare) equilibrated in 20 mM imidazole, 25 mM Tris pH 8.5, 150 mM NaCl, 0.1 mM TCEP, 0.02% $NaN_3$. The protein was further purified on a SUPERDEX S75 column as described above. Following gel filtration, the protein was dialyzed into gel filtration buffer with 5% glycerol. TIP-1 protein quantitation was achieved by using the $A_{280}$ nm experimentally determined extinction coefficient value of 10715 $cm^{-1}*M^{-1}$ (Cushing, et al. (2008) supra). All purified proteins were deemed thermally stable at the temperatures used for in vitro binding measurements by monitoring thermal stability (Cushing, et al. (2008) supra).

Peptide Synthesis.

All peptides, except those used in peptide arrays experiments, were synthesized and HPLC-purified by Tufts Peptide Core Facility. Peptides with N-terminally coupled fluorescein (via an aminohexanoic acid linker) are denoted by a "F*-" prefix. Biotin-conjugated peptides ("BT") were N-terminally coupled via an WrFKK (SEQ ID NO:34) linker sequence (r=D-Arg).

Cell Culture.

CFBE41o-cells (Bruscia, et al. (2002) Gene Ther 9:683-685) stably expressing ΔF508-CFTR under the control of a cytomegalovirus promoter (CFBE-ΔF cells; Li, et al. (2006) Am. J. Respir. Cell Mol. Biol. 34:600-608) are described in the art (Bebok, et al. (2005) J. Physiol. 569:601-615). Cells were cultured and switched to MEM containing only penicillin and streptomycin 24 hours before experiments. All cells used in experiments were between passages 15 and 20.

PDZ Pull-Down Assay.

Briefly, pull-down assays were performed by incubating biotin-conjugated peptides or buffer with streptavidin paramagnetic beads (PROMEGA). Excess peptide was removed by washing. Clarified CFBE-AF cell lysates were added to the beads and incubated with rotation for 90 minutes at 4° C. Beads were washed and bound proteins were eluted with buffer, peptide inhibitor, or scrambled peptide. Proteins were separated by SDS-PAGE and immunoblotted. For mass spectrometry identification, SILVERQUEST (Invitrogen) was used to silver stain protein bands according to manufacturer's instructions. Bands were considered to be candidate protein interactors if they were enriched in the specific non-biotinylated peptide-eluted lane (e.g. iCAL36) versus the SCR-eluted lane. Destained protein bands were identified. Confirmation of peptide fragments was from three independent sample submissions, with CAL and TIP-1 positively identified with each submission.

Fluorescence Anisotropy and Peptide Array Experiments.

Peptide fluorescence anisotropy binding studies were performed as described (Cushing, et al. (2008) supra). ΔΔG values were calculated from $K_i$ values. In the case of weak affinity inhibitors ($K_i$>1000 μM), $K_i$ values were estimated. Inverted peptide array experiments were performed as described (Boisguerin, et al. (2004) Chem. Biol. 11:449-459; Boisguerin, et al. (2007) Chembiochem. 8:2302-2307). For TIP-1 peptide array experiments, $His_{10}$ tagged (uncleaved) protein was used to facilitate quantitation.

TIP-1:iCAL36 Crystallization and Data Collection.

iCAL36 was added at a final concentration of 1 mM to purified TIP-1 at 5.5 mg $ml^{-1}$ in 10 mM HEPES pH 7.4, 25 mM NaCl. Initial crystallization conditions were identified for the TIP-1:iCAL36 complex by micro-batch screening at the Hauptman-Woodward Medical Research Institute High-Throughput Screening laboratory (Luft, et al. (2003) J. Struct. Biol. 142:170-179). Crystallization conditions identified by screening were optimized in hanging-drop format at 291 K, by adding 2 μl of the complex in screening buffer (5.5 mg $ml^{-1}$ TIP-1 and 1 mM iCAL36) to 2 μl reservoir solution. The reservoir contained 500 μl solution. Crystals appeared in 2-4 days and continued to grow for up to 14 days. The crystal used for data collection was obtained using 100 mM $NH_4SCN$, 100 mM MES pH 6.0, 36% (w/v) polyethylene glycol (PEG) 1000 as reservoir buffer.

For data collection, the crystal was transferred into cryoprotectant buffer [200 mM $N_{H4}SCN$, 100 mM MES pH 6.0, 30% (w/v) PEG 400. The data set used for structure determination was obtained at 100K, λ=1.0000 Å on beam line X6A at the National Synchrotron Light Source (NSLS) at Brookhaven National Laboratory. Two data sets were collected and later merged; one over a 360° range, using 0.3° frames and an exposure time of 2 seconds per frame, and the second over 60°, using 1° frames, an exposure time of 0.5 seconds per frame, and an aluminum foil filter. Diffraction data were processed using the XDS package. The TIP-1:iCAL36 complex crystallizes in space-group P1 with unit cell dimensions a=27.0, b=34.1, c=66.9 Å, α=79.6°, β=87.1°, γ=89.9°, and diffracted to a resolution of 1.24 Å.

TIP-1:iCAL36 Structure Determination and Refinement.

Molecular replacement was performed using PHENIX (Adams, et al. (2010) Acta Crystallogr. D Biol. Crystallogr. 66:213-221; McCoy, et al. (2007) J. Appl. Crystallogr. 40:658-674), using the TIP-1:β-catenin structure as a template (PDB ID=3DIW; Zhang, et al. (2008) J. Mol. Biol. 384:255-263). The model was built and refined using phenix (Adams, et al. (2010) supra). The final structure has a $R_{work}$=18.0% and $R_{free}$=19.3%. Detailed data collection and refinement statistics are in Table 3.

TABLE 3

| Data Collection | |
|---|---|
| Space Group | P1 |
| Unit cell dimensions: | |
| a, b, c (Å) | 26.97, 34.09, 66.86 |
| α, β, γ (°) | 79.64, 87.15, 89.97 |

TABLE 3-continued

| | |
|---|---|
| Matthews Coefficient (Å³ Da⁻¹) | 2.01 |
| Molecules in ASU (Z) | 2 |
| Solvent content | 0.39 |
| Wavelength (Å) | 0.9181 |
| Resolution[a] (Å) | 19.11-1.24 (1.31-1.24) |
| Unique reflections | 60547 |
| $R_{sym}$[b] | 0.04 (0.27) |
| $<I/\sigma_I>$ | 27.63 (4.29) |
| $R_{mrgd-F}$[c] | 5.5 (43.9) |
| Completeness (%) | 91.3 (70.0) |
| Molecular Replacement | |
| Rotation function search | |
| Peak no. | 0 |
| Log-likelihood gain | 191 |
| Z-score | 15.4 |
| Translation function search | |
| Peak no. | 2 |
| Log-likelihood gain | 749 |
| Z-score | 22.9 |
| Overall log-likelihood gain | 1476 |
| Refinement | |
| Total number of reflections | 60,539 |
| Reflections in the test set | 3,044 |
| $R_{work}$[d]/$R_{free}$[e] | 0.180/0.193 |
| Number of atoms: | |
| Protein | 1,923 |
| Solvent | 256 |
| Ramachandran plot[f] (%) | 92.1/7.9/0/0 |
| $B_{av}$ (Å²) | |
| Protein | 19.75 |
| Solvent | 28.01 |
| Bond length RMSD | 0.005 |
| Bond angle RMSD | 0.985 |

[a]Values in parentheses are for data in the highest-resolution shell.
[b]Rsym = Σhi|I(h) − Ii(h)|/hi Ii(h), where Ii(h) and I(h) values are the i-th and mean measurements of the intensity of reflection h, respectively.
[c]SigAno = <(|F(+) − F(−)|/σ_Δ)>.
[d]Rwork = Σh|Fobs(h) − Fcalc(h)|/Σh Fobs(h), hε {working set}.
[e]Rfree = h_Fobs(h)_Fcalc(h)_/h Fobs(h), hε {test set}.
[f]Core/allowed/generously allowed/disallowed.

TIP-1:iCAL42 and TIP-1:β-catenin Substitution Modeling.

The TIP-1:iCAL36 and TIP-1:β-catenin structures were aligned using PyMOL (RMSD=0.38 Å).

TIP-1:β-catenin Substitution Modeling.

The TIP-1:β-catenin cocrystal structure (PDB ID=3DIW; Zhang, et al. (2008) supra) was used as a template for assessing the observed loss of affinity in the iCAL42 Trp→Leu $P^{-5}$ ligand substitution. The $P^{-5}$ tryptophan was substituted for leucine in WINCOOT (Emsley, et al. (2010) Acta Crystallogr. D Biol. Crystallogr. 66:486-501), and individual PDB files created for the possible rotamers. Each rotamer was evaluated for potential steric clashes and non-optimal bond geometry with MOLPROBITY (Chen, et al. (2010) Acta Crystallogr. D Biol. Crystallo Ussing Chamber gr. 66:12-21).

Measurements.

Short circuit current ($I_{SC}$) measurements were performed. Briefly, 10⁵ cells were seeded onto 12 mm SNAPWELL permeable supports (Corning) and allowed to form polarized monolayers over the course of 9 days. CFBE-AF cells were dosed with 0.5 mM peptide via BIOPORTER (Sigma) 3.5 hour before the start of Ussing chamber measurements. Cells were maintained at 37° C. throughout treatments; the DMSO concentration did not exceed 0.03%. Cells were treated sequentially with 50 μM amiloride, 20 μM forskolin, 50 μM genistein, and 5 μM CFTR$_{inh}$-172 in 5.0 minute intervals. CFTR-specific chloride efflux was computed as the magnitude of $\Delta I_{SC}$ following application of CFTR$_{inh}$-172. Resistances were monitored throughout each experiment to ensure monolayer integrity.

Statistical Analysis.

Values are reported as mean±SD except for Ussing chamber experiments where mean±SEM is reported. Student's one-tailed t-test was used for fluorescence anisotropy binding experiments while the Student's one-tailed paired t-test was used for analysis of Using chamber experiments.

K* Algorithm.

K* computationally searches over protein sequence mutations for a given protein-peptide complex and assigns each sequence a score, called a K* score (Chen, et al. (2009) Proc. Natl. Acad. Sci. 106:3764-3769; Georgiev, et al. (2008) J. Comp. Chem. 29:1527-1542). To compute the score for a given protein-peptide complex sequence, K* evaluates the low-energy conformations for the sequence and uses them to compute a Boltzmann-weighted partition function. Partition functions are computed for each protein binding partner using rotamer-based ensembles defined as $$q_A = \sum_{a \in A} \left[\frac{\exp(-E_a)}{RT}\right], \quad q_B = \sum_{b \in B} \left[\frac{\exp(-E_b)}{RT}\right], \quad q_{AB} = \sum_{ab \in AB} \left[\frac{\exp(-E_{ab})}{RT}\right],$$

where $q_{AB}$ is the partition function for protein A bound to protein B, and $q_A$ and $q_B$ are the partition functions for the unbound proteins, A and B. The K* score is defined as the ratio of partition functions:

$$K^* = \frac{q_{AB}}{q_A q_B},$$

which is an approximation of the protein complex binding constant, $K_A$ (Georgiev, et al. (2008) supra). Sequences are ranked based on their K* score, where sequences with a higher K* score are considered to have a better binding constant for the bound complex.

During a partition function calculation, K* uses dead-end elimination (DEE) to prune side-chain rotamers that provably cannot be part of low-energy structures. K* utilizes the DEE pruning criterion minDEE (Georgiev, et al. (2008) supra), which allows local side-chain rotamer minimization during the search that can relieve clashes that arise when only allowing rigid side-chain placements. The branch-and-bound algorithm A* (Leach & Lemon (1998) Proteins: Struct. Funct. Genet. 33:227-239) is used to enumerate conformations in gap-free order of their minimum energy bounds (Georgiev, et al. (2008) supra). These conformations are then Boltzmann-weighted and incorporated into the partition function. The partition function is computed with respect to the input model (protein structure, energy function, and rotamer library), so the accuracy of the partition function is bounded by the accuracy of the input model.

Computational Designs with K*.

The previously-determined NMR structure of the CAL PDZ domain bound to the C-terminus of CFTR was used to model the binding of CAL to CFTR (Piserchio, et al. (2005) Biochemistry 44:16158-16166). The CFTR peptide in the NMR structure was truncated to the six most C-terminal amino acids and mutated to the amino acid sequence WQTSII (SEQ ID NO:36) to mimic the best peptide hexamer for CAL discovered thus far. An acetyl group was modeled onto the N-terminus of the peptide using restrained molecular dynamics and minimization where the N-terminus of the peptide was allowed to move, while the remainder of the protein complex was restrained using a harmonic potential (Case, et al. (2005) *J. Comp. Chem.* 26:1668-1688). An 8 Å shell around the peptide hexamer was used as the input structure to K*. The four most C-terminal residues, TSII (SEQ ID NO:37), were allowed to mutate to the following residues during the design search: Thr (all amino acids except Pro), Ser (T/S), Ile (all amino acids except Pro), and Ile (I/L/V). In addition, the Probe program (Word, et al. (1999) *J. Mol. Biol.* 285:1711-1733) was used to determine the side-chains on CAL that interact with the CFTR peptide mimic. The nine residues that interact with the peptide, as well as the two most N-terminal residues on the peptide, were allowed to be flexible during the design search. The peptide was allowed to rotate and translate as a rigid body during the search, as previously described for small molecules (Chen, et al. (2009) supra; Georgiev, et al. (2008) supra; Frey, et al. (2010) *Proc. Natl. Acad. Sci. USA* 107:13707-13712). To explore the feasibility of the new algorithms, unless otherwise noted, full partition functions were not computed and a maximum of $10^3$ conformations were allowed to contribute to each partition function.

Rotamer values were taken from the Penultimate Rotamer Library modal values (Lovell, et al. (2000) *Proteins: Struct. Funct. Genet.* 40:389-408). The energy function used to evaluate protein conformations has been previously described (Chen, et al. (2009) supra; Frey, et al. (2010) supra). The energy function, E=vdW+Coul+EEF1, includes a van der Waals term, a Coulombic electrostatics term, and an EEF1 implicit solvation term (Lazaridis & Karplus (1999) *Proteins: Struct. Funct. Genet.* 35:133-152). All design runs used the Amber (Weiner, et al. (1986) *J. Comp. Chem.* 7:230-252) forcefield terms except for one prospective design run, which used the Charmm (Brooks, et al. (1983) *J. Comp. Chem.* 4:187-217) forcefield parameters.

Training of Energy Function Weights.

Previously-determined experimental binding constants (Cushing, et al. (2008) supra) for 16 of CAL's natural ligands were used to train the energy function weight parameters. K* scores were computed for each of the natural ligands. For this training, the CAL-CFTR structure only included the four most C-terminal residues of the peptide inhibitor. A gradient descent method was used to optimize the correlation between the K* scores and the experimental $K_i^{-1}$ values.

Peptide Array Comparison.

The peptide array data was composed of 6223 C-termini (11-mers) from human proteins. The array was incubated with the CAL PDZ domain in order to determine binding of CAL to the 11-mers. The K* algorithm was used to evaluate 4-mer structural models of the peptide-array sequences to verify the accuracy of the predictions.

To compare the array data with the K* predictions, the quantitative array data, measured in biochemical light units (BLUs), was converted into a binary yes/no CAL binding event. In other words, by setting a binding cutoff on the peptide array, each sequence was classified as either a CAL binder or non-binder. The cutoff value was chosen as three standard deviations away from the average BLU value of the array.

Prospective Computational Predictions.

K* was used to search over all peptide sequences within the CAL PDZ domain sequence motif to find new CAL peptide inhibitors. For computational efficiency, the number of conformations enumerated by A* for each partition function was limited to $10^3$ conformations. Two sets of peptides (promising designs and poorly ranked designs) were chosen to be experimentally validated.

In order to choose the most promising peptide inhibitors, a second K* design was performed, where K* scores for the top 30 sequences were re-calculated with the number of enumerated conformations per partition function increased to $10^5$. Several top-ranked sequences were chosen to be experimentally tested. First, the top seven ranked sequences from the second run were chosen. In addition, two sequences that greatly increased in ranking from the first to second run (rank 29 to 9, and rank 28 to 11) were chosen as well. Finally, a K* run was conducted using Charmm forcefield parameters instead of Amber parameters. Two sequences that scored high on both the Amber and Charmm runs were chosen to be experimentally tested as well.

The poorly-ranked designs were chosen to minimize the sequence similarity among the set of poorly-ranked peptides. First, the worst-ranked peptide was chosen and added to initialize the set of negative sequences. Next, sequences were successively chosen from the worst 200 K* ranked sequences and added to the set in order to maximize the amino acid sequence diversity with all the sequences already in the set. The similarity between two sequences was determined using the PAM-30 similarity matrix (Dayhoff, et al. (1978) *Nat. Biomed. Res. Found.* 5:345-352). In total, 23 (eleven top-ranked and twelve poorly-ranked) K*-computed peptide inhibitor sequences were experimentally tested.

Experimental Procedure. The experimental inhibitory constants of top- and poorly-ranked peptide sequences from the K* CAL-CFTR design were experimentally determined. As a control, the best known peptide hexamer was also retested. The corresponding N-terminally acetylated peptides were purchased from NEO Bio-Science (Cambridge, Mass.) and the $K_i$ values for the peptides were detected using fluorescence polarization. Briefly, the CAL PDZ domain was incubated with a labeled peptide of known binding affinity. Each peptide inhibitor was serially diluted and the protein-peptide mixture was added to each dilution. Finally, the amount of competitive inhibition was tracked using residual fluorescence polarization.

The Ussing chamber experiments were performed as described herein. Polarized monolayers of patient-derived bronchial epithelial cells, CFBE-Δ cells, were treated with peptide and BIOPORTER (Gene Therapy Systems; San Diego, Calif.) delivery agent. Peptide inhibitor was applied to the monolayer and the short circuit currents ($I_{SC}$) were monitored in Ussing chambers. ΔF508-CFTR chloride flux was measured as the change in $I_{SC}$ when the CFTR specific inhibitor, $CFTR_{inh}$-172 (Taddel, et al. (2004) *FEBS let.* 558:52-56; Ma, et al. (2002) *J. Clin. Invest.* 110:1651-1658), was applied to the cell monolayer.

Example 2

Identification of Selective Inhibitors of the CAL and CFTR Interaction

Using peptide-array screening and fluorescence-polarization binding assays, a series of peptide sequences were identified that bind CAL progressively more tightly than CAL binds to CFTR, and that in parallel bind NHERF1 and NHERF2 progressively more weakly than these proteins bind to CFTR.

To test the ability of CAL inhibitors to rescue CFTR, cultured airway epithelial cells (cell line CFBE410-, derived from a CF patient's Bronchial Epithelium) were grown on filters, permitting formation of polarized cell monolayers similar to those found in epithelial tissues. The CFBE41o-cell line is well-recognized as an airway epithelial model system for the study of CF processes. These cells express the most common disease mutant associated with CF, ΔF508-CFTR, which is characterized by the loss of a single amino acid codon at position 508 of CFTR. Roughly 50% of CF patients are homozygous for ΔF508-CFTR, and another 40% are heterozygotes for this allele. Functional rescue of ΔF508-CFTR therefore has the potential to alleviate symptoms in up to 90% of CF patients. Although very little ΔF508-CFTR protein is synthesized in the absence of intervention, the protein itself retains some functional activity. If rescued and stabilized it can restore physiological CFTR activity, potentially reversing the processes that lead to chronic lung infection, and ultimately death, in most CF patients.

When introduced into CFBE41o-cells using commercial peptide transfection reagents, representative peptide and peptidomimetic compounds were able to increase the amount of ΔF508-CFTR protein at the apical membrane and to increase the CFTR-mediated chloride efflux across the monolayers. The magnitude of the functional rescue correlated with the selectivity of the peptides for CAL vs. NHERF1 and NHERF2; the more selective the peptide for the CAL binding site, the more effective it was at enhancing chloride efflux.

Furthermore, when used in combination with a compound that enhances the biosynthesis of ΔF508-CFTR (a "corrector"), the instant inhibitors showed an additive effect, comparable in magnitude to that of the corrector compound.

Although compounds have previously been designed to enhance the synthesis and/or chloride-channel activity of CFTR, the instant inhibitors were designed to stabilize mutant CFTR protein that has already been synthesized within the cell and successfully transported to the cell surface. The peptides and peptidomimetics disclosed herein provide a basis for further optimization of CAL inhibitor properties in terms of affinity and selectivity for CAL, in vivo proteolytic stability, cellular uptake, and ADME characteristics.

Example 3

Assays for Assessing Activity of Selective Inhibitors

Agents of the present invention can be assayed for their ability to stimulate chloride transport in epithelial tissues. Such transport may result in secretion or absorption of chloride ions. The ability to stimulate chloride transport may be assessed using any of a variety of systems. For example, in vitro assays using a mammalian trachea or a cell line, such as the permanent airway cell line Calu-3 (ATCC Accession Number HTB55) may be employed. Alternatively, the ability to stimulate chloride transport may be evaluated within an in vivo assay employing a mammalian nasal epithelium. In general, the ability to stimulate chloride transport may be assessed by evaluating CFTR-mediated currents across a membrane by employing standard Ussing chamber (see Ussing & Zehrahn (1951) *Acta. Physiol. Scand.* 23:110-127) or nasal potential difference measurements (see Knowles, et al. (1995) *Hum. Gene Therapy* 6:445-455). Within such assays, an agent that stimulates a statistically significant increase in chloride transport at a concentration of about 1-300 μM is said to stimulate chloride transport.

Within one in vitro assay, the level of chloride transport may be evaluated using mammalian pulmonary cell lines, such as Calu-3 cells, or primary bovine tracheal cultures. In general, such assays employ cell monolayers, which may be prepared by standard cell culture techniques. Within such systems, CFTR-mediated chloride current may be monitored in an Ussing chamber using intact epithelia. Alternatively, chloride transport may be evaluated using epithelial tissue in which the basolateral membrane is permeabilized with *Staphylococcus aureus* α-toxin, and in which a chloride gradient is imposed across the apical membrane (see Illek, et al. (1996) *Am. J. Physiol.* 270:C265-75). In either system, chloride transport is evaluated in the presence and absence of a test agent, and those compounds that stimulate chloride may be used within the methods provided herein.

Within another in vitro assay for evaluating chloride transport, cells, such as NIH 3T3 fibroblasts, are transfected with a CFTR gene having a mutation associated with cystic fibrosis (e.g., ΔF508-CFTR) using well known techniques (see Anderson, et al. (1991) *Science* 25:679-682). The effect of an agent on chloride transport in such cells is then evaluated by monitoring CFTR-mediated currents using the patch clamp method (see Hamill, et al. (1981) *Pflugers Arch.* 391:85-100) with and without agent.

Alternatively, such assays may be performed using a mammalian trachea, such as a primary cow tracheal epithelium using the Ussing chamber technique as described above. Such assays are performed in the presence and absence of a test agent to identify agents that stimulate chloride transport.

Example 4

Single-Domain Specificity of a CAL PDZ Inhibitor that Rescues ΔF508-CFTR iCAL36 is a Highly Selective PDZ Inhibitor. To determine the full spectrum of PDZ domains inhibited by iCAL36 (sequence: ANSRWPTSII; SEQ ID NO:20) in epithelial cells, a pull-down/mass-spectrometry assay for iCAL36 interactors was developed. As bait, an N-terminally biotinylated (BT-) version of iCAL36 was used, which retained the binding profile of the decamer. BT-iCAL36 was coupled to streptavidin beads and incubated with whole-cell lysates (WCL) from human cystic fibrosis bronchial epithelial cells expressing £F508-CFTR (CFBE-ΔF cells). Mass spectrometry revealed only two PDZ proteins among the "prey" proteins that were enriched in iCAL36 vs. control eluates. CAL was identified with good peptide coverage. The second PDZ sequence identified by mass-spectrometry was the Tax-interacting protein-1 (TIP-1). Both interactions were validated using WCL pull-downs and immunoblot analysis. Thus, although initially engineered to avoid interactions only with the NHERF1 and NHERF2 PDZ domains, iCAL36 has a strikingly selective interaction profile, robustly engaging only a single "off-target" protein among the entire spectrum of PDZ proteins present in airway epithelial cell lysates.

The significant enrichment of the iCAL36-eluted bands over the inputs, especially in the case of TIP-1, was consistent with a potent interaction. To quantify its strength relative to the on-target binding of CAL, recombinant expression and purification protocols were developed for the TIP-1 PDZ domain and its interaction with a fluoresceinated iCAL36 peptide (F*-iCAL36) was monitored by means of fluorescence polarization (FP). Titration revealed a strong, dose- and sequence-dependent binding isotherm, with a fitted $K_d$ of 0.54 μM. Surprisingly, TIP-1 actually bound F*-iCAL36 2.5-fold more tightly than CAL ($K_d$=1.3 μM), and its submicromolar interaction placed it at the high-affinity end of the spectrum of PDZ:peptide interactions (Stiffler et al. (2007) *Science* 317:364-369).

An unusual protein composed almost entirely of a single PDZ domain, TIP-1 has been implicated in negatively regulating the Wnt signaling pathway by sequestering β-catenin (Kanamori, et al. (2003) *J. Biol. Chem.* 278:38758-38764). Recent reports also suggest TIP-1 may play a role in regulating the surface expression of membrane proteins, including Kir 2.3 (Alewine, et al. (2006) *Mol. Biol. Cell* 17:4200-4211). Thus, despite the excellent overall specificity of iCAL36, its off-target interaction with TIP-1 could potentially have contributed to its effects on CFTR stability. To resolve this target ambiguity, and to test the ability to achieve true single-PDZ specificity, CAL inhibitors were designed without TIP-1 affinity.

Sequence Determinants of the iCAL36:TIP-1 Interaction.

As a basis for eliminating the off-target interaction, parallel structural and biochemical approaches were undertaken to understand the contributions of individual iCAL36 side chains to TIP-1 binding. To visualize the stereochemistry of binding, the structure of the TIP-1:iCAL36 complex was determined by X-ray crystallography. The iCAL36 peptide adopted a canonical PDZ-binding conformation in the TIP-1 binding pocket, with standard C-terminal carboxylate, $P^0$ and $P^{-2}$ interactions. In addition, the $P^{-5}$ side chain was bound within a deep, hydrophobic pocket that provided excellent stereochemical complementarity to the planar Trp-conjugated ring system. In contrast, the structure of the CAL PDZ domain showed no equivalent pocket.

In order to assess the free-energy contribution of each side chain to the interaction, substitutional analysis (SubAna) was performed by synthesizing peptide arrays containing the iCAL36 sequence with the amino acid at each position individually replaced with all 19 natural alternatives. Consistent with the stereochemistry of the interaction, the binding patterns of the CAL and TIP-1 PDZ domains also highlighted the importance of the $P^{-5}$ Trp side chain to the off-target binding affinity of iCAL36. $P^{-5}$ substitution with any other natural amino acid abrogated TIP-1 binding, whereas multiple substitutions were tolerated at other positions along the iCAL36 sequence. In contrast, CAL binding was retained for multiple substitutions at both the $P^{-5}$ position and elsewhere in the sequence. Both the biochemical and structural data thus indicated that the affinity of TIP-1 for iCAL36 was tightly focused on the $P^{-5}$ position, whereas CAL's affinity was more broadly distributed along the length of the peptide.

To identify the sources of iCAL36 affinity for TIP-1 in more detail, the TIP-1 binding affinity of the somatostatin receptor subtype 5 (SSR5) C-terminal peptide (ANGLM-QTSKL; SEQ ID NO:38) was also determined, which was the starting sequence for the original peptide engineering effort. Using F*-iCAL36 as a high-affinity reporter peptide, an FP displacement assay revealed that the SSR5 sequence interacted with TIP-1 even though it had a Met at the $P^{-5}$ position, a substitution that abrogated TIP-1 binding in the context of the iCAL36 sequence. In comparison to unlabeled iCAL36, which binds TIP-1 with a $K_{i\,of}1.8\,\mu M$, the $K_i$ for the unlabeled SSR5 peptide binding was 130 µM. Taken together, these data indicate that both the baseline affinity of the SSR5 starting sequence and the $P^{-5}$ Trp represented potential contributors to the high affinity of the off-target interaction.

A Stereochemical Achilles' Heel.

The ability of the combinatorial peptide-array/FP counter-screening paradigm to improve the iCAL selectivity profile was analyzed. CombLib peptide arrays, in which all 400 possible pairs of amino acids were inserted into positions $P^{-5}$ and $P^{-4}$ had already been evaluated for binding to the CAL and NHERF PDZ domains as described herein. A comparable CombLib was subsequently prepared and surveyed for TIP-1 binding. In the framework of the iCAL36 sequence, TIP-1 binding was strictly confined to peptides that included an aromatic residue at $P^{-5}$. Parallel CombLibs based on the full iCAL36 sequence confirmed that the $P^{-5}$ and $P^{-4}$ preferences were relatively independent of upstream sequence context.

Comparison with published arrays identified a number of combinations that bound CAL, but did not bind TIP-1 or any of the NHERF domains studied. Among these was a Leu/Pro combination. The SubAna arrays showed that the CAL-binding signal of the $P^{-5}$ Leu substitution was comparable to those of the strongest Trp/Xaa combinations. Separate SubAna arrays based on the new sequence (iCAL42; ANSRLPTSII; SEQ ID NO:21) confirmed that the CAL PDZ binding preferences were largely retained. Underscoring the critical contribution of the $P^{-5}$ Trp side chain, TIP-1 binding was abrogated for all single substitutions of the Leu-based iCAL42 sequence except for the Leu/Trp revertant.

In order to quantitate the impact of the $P^{-5}$ Leu substitution and to assess inhibitory potential at high peptide concentrations, FP displacement assays were performed. Consistent with the qualitative data, CAL displacement isotherms showed that iCAL42 retained robust CAL PDZ affinity, with a fitted $K_i$ value of 53 µM, only three-fold weaker than unlabeled iCAL36. The NHERF CombLib preferences were also validated: iCAL42 failed to bind any of the four NHERF1 or NHERF2 PDZ domains with appreciable affinity. Critically, the iCAL42 displacement isotherm for TIP-1 was also essentially indistinguishable from the vehicle control up to millimolar peptide concentrations, representing a >1500-fold decrease in binding affinity. Thus, in the context of the iCAL36 sequence, the $P^{-5}$ side chain acted as a single-site TIP-1 affinity switch.

Compared to the >1500-fold loss of affinity achieved by a Trp/Leu substitution in iCAL36, a $P^{-5}$ Trp/Ala substitution in the β-catenin C-terminus caused only a 100-fold loss of TIP-1 affinity (Zhang, et al. (2008) supra). The greater sensitivity of the iCAL36 sequence could be due to the orientation of its Trp side chain within the TIP-1 binding pocket, which differs from that observed in the TIP-1:β-catenin complex (Zhang, et al. (2008) supra). Alternatively, the differential free-energy change could be due to the different replacement side-chains (Ala vs. Leu). In particular, analysis of the TIP-1 $P^{-5}$ pocket suggests that it could not readily accommodate the larger branched Leu side chain at this position. To determine the relative contributions of Trp affinity and/or Leu incompatibility to the iCAL42 binding energy, a $P^{-5}$ alanine mutant of iCAL36 was synthesized and its binding was tested by FP displacement. The ANSRAPTSII sequence (SEQ ID NO:22) exhibited a similar lack of affinity for TIP-1 as did iCAL42. Thus, it appeared that the thermodynamic impact of the $P^{-5}$ substitution on the TIP-1:iCAL36 interaction primarily reflected the loss of the Trp side chain in stabilizing this complex, rather than a specific incompatibility of Leu.

iCAL42 is a Single-PDZ Inhibitor of Endogenous CAL.

Exploiting the localized vulnerability of the TIP-1 binding site for iCAL36, a dramatic increase in inhibitor selectivity against known off-target interactions was generated, as measured by the difference between the free energy of a given peptide binding to the CAL PDZ domain and the free energy of the same peptide binding to the highest affinity alternative among the NHERF and TIP-1 PDZ domains (ΔΔG). The SSR5 starting sequence bound CAL almost exactly as tightly as the closest NHERF1 or NHERF2 domain, N2P2 (ΔΔG-CAL-best=+0.1 kcal/mol). While the binding free energy of iCAL36 for CAL was much more favorable than for the NHERF PDZ domains (ΔΔG=−3.3 kcal/mol), it was actually 1.0 kcal/mole less favorable than for TIP-1 (ΔΔG=+1.0 kcal/mol). iCAL42 reversed this trend, binding CAL with a free energy that was substantially more favorable than any of the other partners (ΔΔG=−2.5 kcal/mol). Thus, the reward for a five-fold reduction in CAL binding affinity was a 60-fold difference relative to the $K_i$ of the PDZ domain with the next highest affinity.

To validate these observations for full-length proteins in the presence of potential physiological accessory proteins, a WCL pull-down assay was used, together with a biotinylated analog of iCAL42, BT-iCAL42. The FP competition assay was used to ensure that the selectivity profile was not compromised by the addition the N-terminal biotin linker. As expected, BT-iCAL42 bound CAL robustly ($K_i$=9.2 µM), but exhibited no appreciable binding for the NHERF and TIP-1 PDZ domains. In a WCL pull-down immunoassay, BT-iCAL42 was used as bait, and captured prey proteins were eluted by displacement with unlabeled iCAL42. When probed by western blot analysis, full-length CAL was clearly identified, but neither NHERF1, NHERF2, NHERF3, nor TIP-1 were observed.

To assess the possibility that the Trp→Leu substitution might have generated unanticipated off-target interactions, in analogy to that originally seen for iCAL36 with TIP-1, the BT-iCAL42 pull-down assay was repeated and putative interactors were resolved by TCA precipitation, SDS-PAGE, and silver staining. Aside from a modest enrichment of CAL, no protein bands were enriched in the iCAL42 eluate compared to the scrambled-peptide control eluate; nevertheless, all major bands were submitted for mass-spectrometric analysis. Consistent with western blot analysis, endogenous CAL was again clearly identified. Moreover, when the stringency of the pull-down assay was reduced, there were no other PDZ-domain containing protein in the eluate. Based on these data, among the PDZ proteins expressed in CFBE-ΔF epithelial cells, CAL was the only one with appreciable affinity for iCAL42.

F*-iCAL42 Enhances CFTR-Mediated Cl$^{-1}$ Secretion.

The strict selectivity of iCAL42 was further used to test whether the off-target TIP-1 interaction might contribute to the ΔF508-CFTR rescue seen with iCAL36. For these studies, the enhanced CAL selectivity of decapeptides carrying an N-terminal fluorescein moiety was exploited. For TIP-1, the affinity of F*-iCAL36 was only three-fold stronger than that of unlabeled iCAL36, compared to a 13-fold increase for CAL. Therefore, an N-terminally fluoresceinated version of iCAL42 (F*-iCAL42) was synthesized and binding against both CAL and TIP-1 was analyzed. In the context of the iCAL42 sequence, the addition of the N-terminal fluorescein moiety produced a five-fold enhancement in CAL affinity. Conversely, the fluoresceinated peptide showed no appreciable binding to TIP-1: at the highest protein concentration tested (150 µM), F*-iCAL42 was essentially indistinguishable from a fluoresceinated scrambled control peptide F*-SCR.

Having validated the affinity profile of the fluoresceinated probe, it was determined whether F*-iCAL42 would be able to rescue ΔF508-CFTR chloride-channel activity as efficiently as F*-iCAL36. In Ussing chamber measurements, F*-iCAL36 and F*-iCAL42 were tested in head-to-head measurements for efficacy versus the scrambled control peptide, F*-SCR. The results of this analysis indicated that F*-iCAL36 increased the CFTR$_{inh}$-172-sensitive short-circuit current ($\Delta I_{SC}$) by 10.7% (p=0.0016; n=10). Treatment of CFBE-ΔF cells with F*-iCAL42 yielded a 12.5% increase (p=0.0013; n=10) in $\Delta I_{SC}$. Thus, F*-iCAL42 was at least as efficacious as F*-iCAL36, suggesting that TIP-1 inhibition was not a substantial component of iCAL-mediated chloride-channel rescue.

Example 5

Computational Design of a PDZ Domain Peptide Inhibitor that Rescues CFTR Activity The K* algorithm was applied to the CAL-CFTR system to find a peptide inhibitor that acted as a biologically-active stabilizer of ΔF508-CFTR. First, new mathematical proofs were developed to show that K* could maintain provable guarantees for protein-peptide interaction design searches. To validate the design methodology, the K* algorithm was applied retrospectively to predict peptide-array binding data. The retrospective test showed K* was able to enrich for peptide inhibitors. K* was then used to prospectively find new peptide inhibitors of CAL. The top predicted sequences were experimentally validated and it was determined that they all bind CAL with µM affinity. Finally, Ussing chamber experiments showed that the best designed peptide rescued ΔF508-CFTR function in bronchial epithelial cells.

Extension of K* to Mutations/Flexibility on Two Protein Strands.

K* relies on the mathematically provable guarantees of each of its steps to compute an accurate K* score. If heuristic steps were used to find the low energy conformations, it could not be guaranteed that all the low energy conformations were found and the ability to calculate a provably-good ε-approximation (where ε is user-defined) to each partition function for the design system would be lost. Because of the provable aspects of K*, if K* makes an errant prediction, it can be certain that it is due to an inaccuracy in the input model and not a problem (such as inadequate optimization) with the search algorithm. This makes it substantially easier to improve the model based on experimental feedback (see Training of Energy Function Weights of Example 1).

Initially, it had to be ensured that the mathematical framework of K* could be extended to cover larger systems. For large designs such as protein-peptide interactions, the provable guarantees of K* no longer hold as they do for small design systems. Specifically, the previous K* proofs (Georgiev, et al. (2008) supra) for intermutation pruning and guaranteeing the accuracy of the K* score, relied on properties of small molecule design systems that are not true for protein-peptide interactions. It was therefore shown that it was possible to improve the K* algorithm to maintain these critical provable guarantees. As a result, systems where both binding partners in the protein complex were flexible or mutable during the search could be accurately studied using K*.

"Intermutation pruning" uses computed partition functions to truncate the conformation enumeration process for design sequences when they will provably fail to achieve a K* score close to the best K* score. To show that an intermutation pruning criterion (Georgiev, et al. (2008) supra) existed for protein-peptide interaction design, a halting condition was sought for the conformation enumeration such that it was known that an ε-approximation to the bound partition function was provided for a given protein complex. First it was observed: $K_j \geq \gamma K_o$, where $K_j$ was the K* score of the current sequence, $K_o$ was the best score observed so far, and γ was a user-selected parameter. In the following lemma, n was the number of conformations in the search that remained to be computed, k was the number of conformations that had been pruned from the search with DEE, $E_0$ was the lower energy bound on all pruned conformations, R was the universal gas constant, and T was the temperature. The full partition function for the protein-protein complex, and unbound proteins were $q_{AB}$, $q_A$, and $q_B$, respectively, while $q_{\hat{A}\hat{B}}$, $q_{\hat{A}}$, and $q_{\hat{B}}$ denoted the current calculated value of the partition functions during the computational search.

Lemma 1.

If the lower bound $E_t$ on the minimized energy of the $(m+1)^{th}$ conformation returned by A* satisfied $E_t \geq -RT(\ln(\gamma \epsilon K_o q_A q_B - k \exp(-E_0/RT)) - \ln n)$, then the partition function computation could be halted, with $q_{AB}$ guaranteed to be an $\epsilon$-approximation to the true partition function, $q_{AB}^*$, for a mutation sequence whose score $K_i$ satisfied $K_i \geq \gamma K_o$.

This lemma showed that even when designing for protein-protein interactions, there existed a sequence pruning criteron during the K* search.

It was then shown that a provable guarantee on the accuracy of the K* score could be obtained for each protein conformation. Since both partition functions were $\epsilon$-approximations, an $\epsilon$-approximation to the K* score could no longer be obtained, but rather the following:

Lemma 2.

When mutations (or flexible residues) were allowed on both strands in a computational design, the computed K* score was a $\sigma$-approximation to the actual K* score, where $\sigma = \epsilon(2-\epsilon)$.

Since neither of the protein complex partition functions were calculated fully, the K* score approximation was a $2\epsilon$-approximation as opposed to the $\epsilon$-approximation for small molecule designs. This implied that better partition function approximations must be computed to maintain the same level of K* score approximation. Nevertheless, the fact that the K* score could still be provably approximated, conferred all the advantages of a provable algorithm as stated above.

Retrospective Validation of the K* Algorithm.

K* predictions were made for peptide sequences from a CAL peptide-array. The peptide-array binding data were used to validate the peptide inhibitor predictions. The resulting receiver operating curve (ROC) when comparing the K* scores to the CAL binding of the peptide array had an area under the curve (AUC) of 0.84, which showed that K* greatly enriched for peptides that bind CAL.

Considering if a prospective test were being conducted and the top 30 K*-ranked sequences were being tested, according to the peptide array, 11 of the top 30 sequences would be found to bind CAL. Notably, this was a 20-fold increase over the number of binders that would be expected to be found if the binding sequences were distributed randomly in the rankings.

Based on previous studies (Reynolds, et al. (2008) *J. Mol. Biol.* 382:1265-1275), CAL was known to bind the canonical sequence motif: X-S/T-X-L/V/I (SEQ ID NO:39). Therefore, a much more stringent test of the K* design algorithm was to determine the degree to which K* enriched for binders if the peptide array was restrict to sequences that matched the known CAL sequence motif. With this new restriction, K* was still able to significantly enrich for CAL peptide binders producing a ROC with an AUC of 0.71. When considering the top 30 K* ranked sequences, 17 of the sequences were binders, which resulted in a 2-fold increase over the expected random distribution.

Prospective Design of CAL Peptide Inhibitors.

Since K* was able to successfully enrich for CAL binders based on peptide array data, K* was then used to prospectively find novel CAL peptide inhibitors. The K* algorithm was used to search over 2166 possible peptide hexamer inhibitors that had an N-terminal W-Q pair followed by four residues that matched the CAL PDZ sequence motif. The top-ranked sequences were chosen to be experimentally validated. The $K_i$ value for each peptide hexamer was determined using fluorescence polarization.

All of the top-ranked inhibitors were novel and none had been predicted or experimentally tested before. Unexpectedly, all of the top predicted peptides bound CAL with high affinity ($\Delta G_{binding}$ in the range of −8 to −6 kcal/mol). The best binding predicted peptide (kCAL01, WQVTRV; SEQ ID NO:23) had a $K_i$ of 2.1 µM. For comparison, the $K_i$ for the wild-type CFTR sequence (TEEEVQDTRL; SEQ ID NO:40) is 690 µM and the highest known affinity natural ligand (ANGLMQTSKL; SEQ ID NO:38) for CAL is 37 µM. Using the K* design algorithm, a peptide inhibitor with 331-fold higher affinity was obtained. Thus, the design algorithm successfully identified high affinity peptide inhibitors of the CAL PDZ domain.

The highest-affinity CAL-binding peptide hexamer (iCAL35, WQTSII; SEQ ID NO:36) identified through SPOT arrays had a $K_i$ of 14.8 µM. Seven of the eleven top tested sequences showed an improvement in binding compared to iCAL35, and kCAL01 showed a 7-fold improvement over iCAL35. The best inhibitor found through the SPOT array screens involved a fluorescein group modification to a peptide decamer (F*-iCAL36, F*-ANRSWPTSII (SEQ ID NO:19), $K_d$=1.3 µM). kCAL01 rivaled this binding affinity despite the computational search library restriction to only allow amino acids and hexamer sequences. Critically, at nearly half the size (830 Da) of F*-iCAL36, kCAL01 had approximately twice the binding efficiency (ratio of inhibitor potency to size) of F*-iCAL36 and was much closer in size to typical drugs.

Furthermore, the tight binding of the top-ranked sequences was not merely a consequence of the underlying CAL-binding motif used to select candidate sequences for evaluation. To confirm this, a set of poorly-ranked sequences was synthesized and their CAL-binding affinity was experimentally evaluated. Almost all of the poorly-ranked sequences bound CAL, consistent with their motifs. Reflecting the enrichment of CAL binders in the pool, the two poorly ranked peptides with the highest affinities ($K_i$=20 µM and 27 µM, respectively) were indeed close to the affinity of the weakest top-ranked sequence ($K_i$=18 µM). However, all of the poorly ranked peptides bound CAL more weakly than any of the top-ranked sequences, and none of them had improved affinity relative to prior biochemical efforts. Thus, K* was a powerful filter, efficiently selecting tight binders from a pool of sequences with baseline affinity for the target.

To determine the importance of the ensemble-based K* rankings, the predictions were compared to two single-structure GMEC-based methods, minDEE (Georgiev, et al. (2008) supra), and rigid-rotamer DEE (rigidDEE) (Gordon, et al. (2003) *J. Comp. Chem.* 24:232-243). Both minDEE and rigidDEE were run with the same parameters as the K* designs, except that the energies were normalized with model compounds as in Lippow, et al. ((2007) *Nat. Biotech.* 25:1171-1176). The top 30 sequences from minDEE and rigidDEE were compared and no sequences in common were observed. In addition, when the top 30 rigidDEE and minDEE results were compared to the top K* designs, it was found that they had only three and four sequences in common, respectively. If only GMEC-based approaches were used instead of K*, most of the experimentally successful sequences would not have been predicted, including the best inhibitor kCAL01. In addition, the overall sequence rankings showed a very poor correlation between the minDEE and K* predictions; the same was true of the rigidDEE and K* predictions ($R^2$=0.1 and 0.09, respectively).

Biological Activity of the Best Designed Peptide Inhibitor.

All of the top-predicted inhibitors successfully bound CAL. This implied that the inhibitors could disrupt the degradation pathway of CFTR. However, to restore CFTR function in epithelial cells, the inhibitor must be specific for CAL and not bind other CFTR trafficking proteins. Interestingly, the top-binding predicted peptide contained a β-branched C-terminal residue (Val) that was preferred by CAL, but not by NHERF PDZ domains.

The ability of the top designed peptide, kCAL01, to restore ΔF508-CFTR function was determined by measuring ΔF508-CFTR-mediated chloride efflux in cystic fibrosis patient-derived bronchial cells expressing ΔF508-CFTR (CFBE-AF) using an Ussing chamber. This analysis compared ΔF508-CFTR chloride flux for a control peptide (kCAL31; WQDSGI (SEQ ID NO:41); no CAL binding expected), iCAL35, and kCAL01. While there was only a slight improvement in chloride flux for iCAL35 over the control peptide (4%), the designed peptide kCAL01 exhibited a much larger increase (12%). The 12% increase in ΔF508-CFTR chloride efflux was similar to the rescue of activity when using the selective peptide F*-iCAL36. Thus, the designed peptide kCAL01 was biologically active and of use in inhibiting the interaction between CAL and CFTR.

What is claimed is:

1. A method for increasing cell surface expression of a degradation-prone Cystic Fibrosis Transmembrane Conductance Regulator (CFTR) protein comprising contacting a cell expressing a degradation-prone CFTR with an effective amount of a peptide comprising the amino acid sequence of (M/F/L/A/W)-(Q/P/F)-(S/T)-(S/T)-(K/I)-I (SEQ ID NO:1) or SEQ ID NO:24, or a derivative or peptidomimetic thereof, that selectively inhibits the interaction between the degradation-prone CFTR and CFTR-Associated Ligand thereby increasing cell surface expression of the degradation-prone CFTR protein as compared to cell surface expression in the absence of the agent.

2. The method of claim 1, wherein the degradation-prone CFTR is ΔF508 CFTR or R1066C CFTR.

3. The method of claim 1, wherein the peptide, derivative or peptidomimetic is 6 to 20 residues in length.

4. The method of claim 1, wherein the peptide is derivatized with a label, one or more post-translational modifications, and/or a cell-penetrating sequence.

5. The method of claim 1, wherein the peptidomimetic comprising the amino acid sequence of SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33.

6. A method for treating cystic fibrosis comprising administering to a subject in need of treatment an effective amount of a peptide comprising the amino acid sequence of (M/F/L/A/W)-(Q/P/F)-(S/T)-(S/T)-(K/I)-I (SEQ ID NO:1) or SEQ ID NO:24, or a derivative or peptidomimetic thereof, that selectively inhibits the interaction between a degradation-prone Cystic Fibrosis Transmembrane Conductance Regulator (CFTR) and CFTR-Associated Ligand thereby treating the subject's cystic fibrosis.

7. The method of claim 6, wherein the degradation-prone CFTR is ΔF508 CFTR or R1066C CFTR.

8. The method of claim 6, wherein the peptide, derivative or peptidomimetic is 6 to 20 residues in length.

9. The method of claim 6, wherein the peptide is derivatized with a label, one or more post-translational modifications, and/or a cell-penetrating sequence.

10. The method of claim 6, wherein the peptidomimetic comprising the amino acid sequence of SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33.

11. A purified peptide comprising the amino acid sequence of SEQ ID NO:24.

12. A peptidomimetic comprising the amino acid sequence of SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33.

13. A pharmaceutical composition comprising the peptide of claim 11 in admixture with a pharmaceutically acceptable carrier.

14. A pharmaceutical composition comprising the peptidomimetic of claim 12 in admixture with a pharmaceutically acceptable carrier.

* * * * *

SEQUENCE LISTING

```
<160> NUMBER OF SEQ ID NOS: 41

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Met, Phe, Leu, Ala or Trp
<220> FEATURE:
<221> NAME/KEY: MISC_FEATURE
<222> LOCATION: (2)..(2)
<223> OTHER INFORMATION: Xaa denotes Gln, Pro, or Phe
<220> FEATURE:
<221> NAME/KEY: MISC_FEATURE
<222> LOCATION: (3)..(3)
<223> OTHER INFORMATION: Xaa independently denotes Ser, Val or Thr
<220> FEATURE:
<221> NAME/KEY: MISC_FEATURE
<222> LOCATION: (4)..(4)
<223> OTHER INFORMATION: Xaa independently denotes Ser or Thr
<220> FEATURE:
<221> NAME/KEY: MISC_FEATURE
<222> LOCATION: (5)..(5)
<223> OTHER INFORMATION: Xaa denotes Lys or Ile
<220> FEATURE:
<221> NAME/KEY: MISC_FEATURE
<222> LOCATION: (6)..(6)
<223> OTHER INFORMATION: Xaa denotes  Ile or Val.

<400> SEQUENCE: 1

Xaa Xaa Xaa Xaa Xaa Xaa
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Cys Ala Asn Gly Leu Met Gln Thr Ser Lys Ile
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Cys Gly Leu Met Gln Thr Ser Lys Ile
```

```
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Cys Phe Phe Ser Thr Ile Ile
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Cys Phe Phe Thr Ser Ile Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Cys Met Gln Thr Ser Ile Ile
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Cys Met Gln Thr Ser Lys Ile
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Cys Trp Gln Thr Ser Ile Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Cys Trp Pro Thr Ser Ile Ile
1               5
```

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Cys Thr Trp Gln Thr Ser Ile Ile
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Cys Lys Trp Gln Thr Ser Ile Ile
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Pro His Trp Gln Thr Ser Ile Ile
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Phe His Trp Gln Thr Ser Ile Ile
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Ser Arg Trp Gln Thr Ser Ile Ile
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

Cys Ala Asn Ser Arg Trp Gln Thr Ser Ile Ile
1               5                   10

```
<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Gly Leu Trp Pro Thr Ser Ile Ile
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Ser Arg Trp Pro Thr Ser Ile Ile
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Phe Pro Trp Pro Thr Ser Ile Ile
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with fluorescein

<400> SEQUENCE: 19

Ala Asn Ser Arg Trp Pro Thr Ser Ile Ile
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Ala Asn Ser Arg Trp Pro Thr Ser Ile Ile
1               5                   10

<210> SEQ ID NO 21
<211> LENGTH: 10
<212> TYPE: PRT
<213> ORGANISM: Artificial sequence
<220> FEATURE:
<223> OTHER INFORMATION: Synthetic peptide

<400> SEQUENCE: 21
```

```
Ala Asn Ser Arg Leu Pro Thr Ser Ile Ile
1               5                   10
```

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

```
Ala Asn Ser Arg Ala Pro Thr Ser Ile Ile
1               5                   10
```

<210> SEQ ID NO 23
<211> LENGTH: 6
<212> TYPE: PRT
<213> ORGANISM: Artificial sequence
<220> FEATURE:
<223> OTHER INFORMATION: Synthetic peptide

<400> SEQUENCE: 23

```
Trp Gln Val Thr Arg Val
1               5
```

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Met, Phe, Leu, or Ala.
<220> FEATURE:
<221> NAME/KEY: MISC_FEATURE
<222> LOCATION: (2)..(2)
<223> OTHER INFORMATION: Xaa denotes Gln, Pro, or Phe.
<220> FEATURE:
<221> NAME/KEY: MISC_FEATURE
<222> LOCATION: (3)..(3)
<223> OTHER INFORMATION: Xaa denotes Ser, Val or Thr.
<220> FEATURE:
<221> NAME/KEY: MISC_FEATURE
<222> LOCATION: (4)..(4)
<223> OTHER INFORMATION: Xaa denotes Ser or Thr.
<220> FEATURE:
<221> NAME/KEY: MISC_FEATURE
<222> LOCATION: (5)..(5)
<223> OTHER INFORMATION: Xaa denotes Lys, Arg or Ile.
<220> FEATURE:
<221> NAME/KEY: MISC_FEATURE
<222> LOCATION: (6)..(6)
<223> OTHER INFORMATION: Xaa denotes Ile or Val.

<400> SEQUENCE: 24

```
Xaa Xaa Xaa Xaa Xaa Xaa
1               5
```

<210> SEQ ID NO 25
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.
<220> FEATURE:
<221> NAME/KEY: MISC_FEATURE

```
<222> LOCATION: (5)..(5)
<223> OTHER INFORMATION: Modified with fluorescein.

<400> SEQUENCE: 25

Trp Arg Phe Lys Lys Ala Asn Ser Arg Trp Pro Thr Ser Ile Ile
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.

<400> SEQUENCE: 26

Trp Arg Phe Lys Lys Ala Asn Ser Arg Trp Pro Thr Ser Ile Ile
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.
<220> FEATURE:
<221> NAME/KEY: MISC_FEATURE
<222> LOCATION: (5)..(5)
<223> OTHER INFORMATION: Modified with 6-carboxy-X-rhodamine.

<400> SEQUENCE: 27

Trp Arg Phe Lys Lys Ala Asn Ser Arg Trp Pro Thr Ser Ile Ile
1               5                   10                  15

<210> SEQ ID NO 28
<211> LENGTH: 10
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(4)
<223> OTHER INFORMATION: D-amino acid residue.

<400> SEQUENCE: 28

Pro Asn Glu Ala Trp Pro Thr Ser Ile Ile
1               5                   10

<210> SEQ ID NO 29
<211> LENGTH: 10
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: D-amino acid residue.
<220> FEATURE:
<221> NAME/KEY: MISC_FEATURE
<222> LOCATION: (3)..(3)
<223> OTHER INFORMATION: D-amino acid residue.
```

```
<400> SEQUENCE: 29

Phe Asn Ala Arg Trp Gln Thr Ser Ile Ile
1               5                   10

<210> SEQ ID NO 30
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-amino acid residue.

<400> SEQUENCE: 30

Phe Asn Ser Arg Trp Gln Thr Ser Ile Ile
1               5                   10

<210> SEQ ID NO 31
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid residue.

<400> SEQUENCE: 31

Lys Asn Ser Arg Trp Gln Thr Ser Ile Ile
1               5                   10

<210> SEQ ID NO 32
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid residue.

<400> SEQUENCE: 32

Pro Asn Ser Arg Trp Gln Thr Ser Ile Ile
1               5                   10

<210> SEQ ID NO 33
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.

<400> SEQUENCE: 33

Ala Asn Ser Arg Trp Gln Thr Ser Ile Ile
1               5                   10

<210> SEQ ID NO 34
<211> LENGTH: 5
<212> TYPE: PRT
<213> ORGANISM: Artificial sequence
<220> FEATURE:
```

<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.

<400> SEQUENCE: 34

Trp Arg Phe Lys Lys
1               5

<210> SEQ ID NO 35
<211> LENGTH: 7
<212> TYPE: PRT
<213> ORGANISM: Artificial sequence
<220> FEATURE:
<223> OTHER INFORMATION: Synthetic peptide

<400> SEQUENCE: 35

Leu Glu Val Leu Phe Gln Gly
1               5

<210> SEQ ID NO 36
<211> LENGTH: 6
<212> TYPE: PRT
<213> ORGANISM: Artificial sequence
<220> FEATURE:
<223> OTHER INFORMATION: Synthetic peptide

<400> SEQUENCE: 36

Trp Gln Thr Ser Ile Ile
1               5

<210> SEQ ID NO 37
<211> LENGTH: 4
<212> TYPE: PRT
<213> ORGANISM: Artificial sequence
<220> FEATURE:
<223> OTHER INFORMATION: Synthetic peptide

<400> SEQUENCE: 37

Thr Ser Ile Ile
1

<210> SEQ ID NO 38
<211> LENGTH: 10
<212> TYPE: PRT
<213> ORGANISM: Artificial sequence
<220> FEATURE:
<223> OTHER INFORMATION: Synthetic peptide

<400> SEQUENCE: 38

Ala Asn Gly Leu Met Gln Thr Ser Lys Leu
1               5                   10

<210> SEQ ID NO 39
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes any amino acid residue.
<220> FEATURE:
<221> NAME/KEY: MISC_FEATURE
<222> LOCATION: (2)..(2)
<223> OTHER INFORMATION: Xaa denotes Ser or Thr.
<220> FEATURE:

```
<221> NAME/KEY: MISC_FEATURE
<222> LOCATION: (3)..(3)
<223> OTHER INFORMATION: Xaa denotes any amino acid residue.
<220> FEATURE:
<221> NAME/KEY: MISC_FEATURE
<222> LOCATION: (4)..(4)
<223> OTHER INFORMATION: Xaa denotes Leu, Val or Ile.

<400> SEQUENCE: 39

Xaa Xaa Xaa Xaa
1

<210> SEQ ID NO 40
<211> LENGTH: 10
<212> TYPE: PRT
<213> ORGANISM: Artificial sequence
<220> FEATURE:
<223> OTHER INFORMATION: Synthetice peptide

<400> SEQUENCE: 40

Thr Glu Glu Glu Val Gln Asp Thr Arg Leu
1               5                   10

<210> SEQ ID NO 41
<211> LENGTH: 6
<212> TYPE: PRT
<213> ORGANISM: Artificial sequence
<220> FEATURE:
<223> OTHER INFORMATION: Synthetic peptide

<400> SEQUENCE: 41

Trp Gln Asp Ser Gly Ile
1               5
```